United States Patent
Fort et al.

(10) Patent No.: US 9,541,751 B2
(45) Date of Patent: Jan. 10, 2017

(54) METHOD OF OBSERVATION OF THE EMISSION OF LIGHT FROM A SAMPLE BY DYNAMIC OPTICAL MICROSCOPY

(75) Inventors: Emmanuel Fort, Cachan (FR); Sandrine Lévêque-Fort, Cachan (FR); Karla Balaa, Paris (FR); Thomas Barroca, Villejuif (FR)

(73) Assignee: Centre National de la Recherche Scientifique, Paris (FR)

( * ) Notice: Subject to any disclaimer, the term of this patent is extended or adjusted under 35 U.S.C. 154(b) by 417 days.

(21) Appl. No.: 13/881,707

(22) PCT Filed: Oct. 25, 2011

(86) PCT No.: PCT/FR2011/052482
§ 371 (c)(1),
(2), (4) Date: Jul. 8, 2013

(87) PCT Pub. No.: WO2012/056160
PCT Pub. Date: May 3, 2012

(65) Prior Publication Data
US 2013/0278742 A1    Oct. 24, 2013

(30) Foreign Application Priority Data
Oct. 28, 2010 (FR) ...................................... 10 58913

(51) Int. Cl.
*G02B 21/36*    (2006.01)
*G02B 21/00*    (2006.01)
(Continued)

(52) U.S. Cl.
CPC ............. *G02B 21/367* (2013.01); *G02B 5/005* (2013.01); *G02B 21/0088* (2013.01);
(Continued)

(58) Field of Classification Search
CPC ............................ G01N 21/6458; G02B 21/16
See application file for complete search history.

(56) References Cited

U.S. PATENT DOCUMENTS 7,046,359 B2 *    5/2006    Voigt et al. ................... 356/301
2003/0086163 A1 *    5/2003    Aono et al. ................... 359/388
(Continued)

FOREIGN PATENT DOCUMENTS

FR    2 943 428 A1    9/2010

OTHER PUBLICATIONS

Wikipedia, Snell's Law, May 29, 2008, internet p. 1-15.*
(Continued)

*Primary Examiner* — Zhubing Ren
(74) *Attorney, Agent, or Firm* — Marshall, Gerstein & Borun LLP

(57) ABSTRACT

Method for observing an emission of light from a sample in a medium of refractive index nL disposed against a surface of a transparent support of refractive index nS, greater than nL, the emission of light comprising luminous components oriented toward the support and forming an angle θ and including supercritical luminous components and critical or subcritical luminous components, implementing an observation device applying filters to the signal; and transforming the signal into an image zone of the sample Modulation of the signal is carried out, in which components of the emission of light are allowed to pass through so as to obtain image zones, the modulation pertaining to all or some of the collected signals; and at least one useful image zone of the sample is produced by combining image zones, the combination evidencing differences between the image zones related to the modulation.

14 Claims, 5 Drawing Sheets

(51) Int. Cl.
    *G02B 21/33* (2006.01)
    *G02B 5/00* (2006.01)
    *G02B 21/16* (2006.01)
(52) U.S. Cl.
    CPC .............. *G02B 21/16* (2013.01); *G02B 21/33* (2013.01); *G02B 21/361* (2013.01)

(56) References Cited

U.S. PATENT DOCUMENTS

2006/0028718 A1* 2/2006 Seel et al. ...................... 359/385
2007/0263226 A1* 11/2007 Kurtz et al. ................... 356/492
2008/0297787 A1* 12/2008 Knebel ......................... 356/300
2010/0243914 A1 9/2010 Kurzbuch et al.

OTHER PUBLICATIONS

Kurzbuch D. et al., "A biochip reader using super critical angle fluorescence," Sensors and Actuators B, Elsevier Sequoia S.A., vol. 137, No. 1, pp. 1-6, Lausanne, Switzerland, 2009.
Laib, S. et al., "Supercritical angle fluorescence biosensor for the detection of molecular interactions on cellulose-modified glass surfaces," Applied Surface Science, Elsevier, vol. 252, No. 22, pp. 7788-7793, Amsterdam, NL 2006.
Valimaki, H., et al., "A novel platform for highly surface-sensitive fluorescent measurements applying simultaneous total internal reflection excitation and super critical angle detection," Chemical Physics Letters, vol. 473, No. 4-6, pp. 358-362, Amsterdan, NL, 2009.
Ruckstuhl, T., et al., "Supercritical angle fluorescence (SAF) microscopy," Optics Express, OSA (Optical Society of America), vol. 12, No. 18, pp. 4246-4254, Washington DC, 2004.
Search Report for PCT/FR2011/052482, mailed Dec. 29, 2011.

* cited by examiner

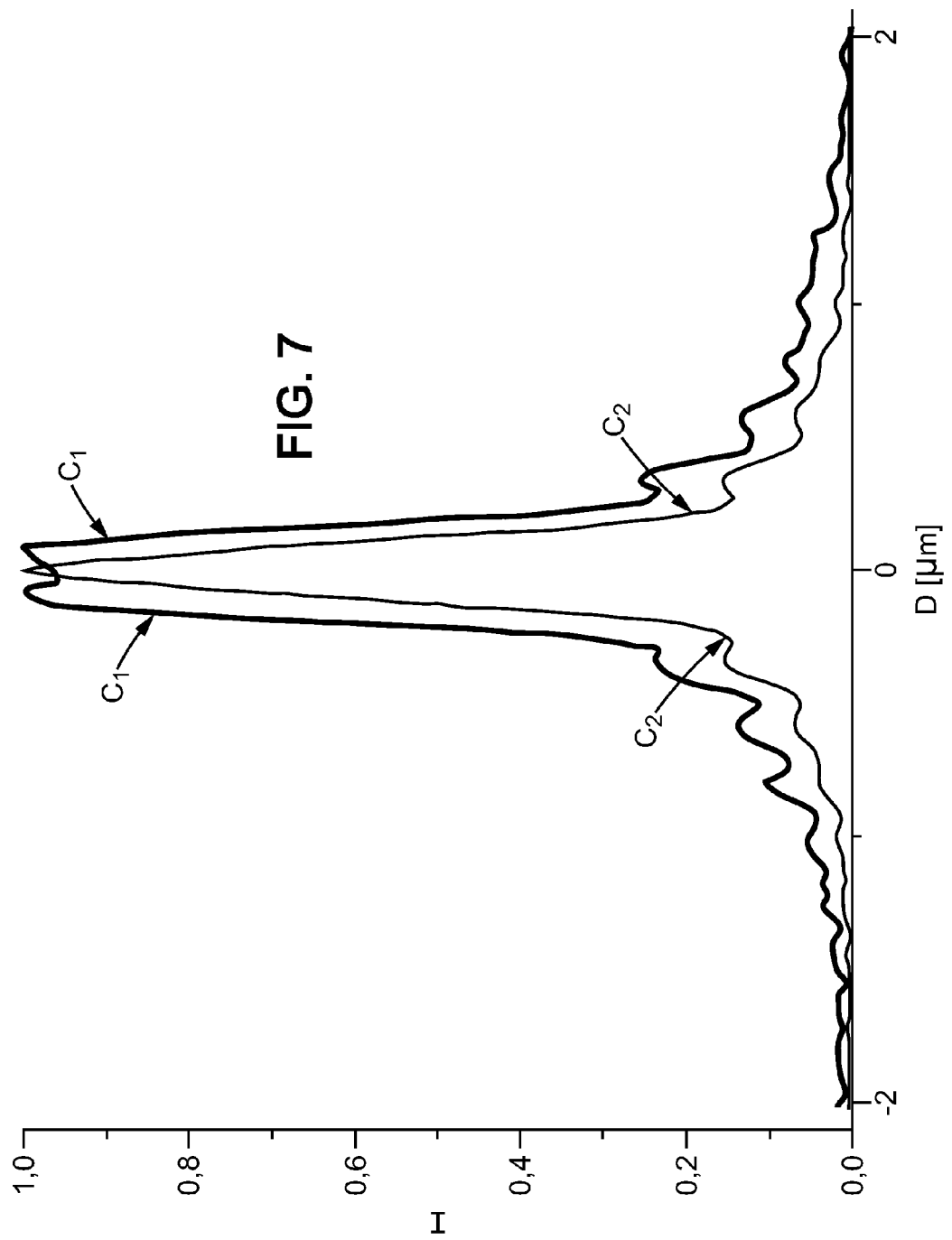

METHOD OF OBSERVATION OF THE EMISSION OF LIGHT FROM A SAMPLE BY DYNAMIC OPTICAL MICROSCOPY

FIELD OF THE INVENTION

The present invention relates to a method of observation of the emission of light from a sample by dynamic optical microscopy.

BACKGROUND OF THE INVENTION

The light from the sample may result from diffusion or fluorescence. Fluorescence microscopy is a technique that takes advantage of the phenomenon of fluorescence in order to observe various compounds. Fluorescence is the property possessed by certain bodies to emit fluorescent light by themselves.

The fluorescence of an observed compound can be primary, if the compound is fluorescent itself (e.g., chlorophyll, oil) or secondary, if the observed compound is marked with a fluorescent substance known as a fluorochrome or fluorescent marker.

In particular in cell biology, a large number of molecular events occurring at the cell surface are studied by fluorescence microscopy, such as cell adhesion, the binding of hormones to receptors in the plasma membrane, the secretion of neurotransmitters as well as membrane dynamics (endocytosis, exocytosis).

A fluorescence microscopy device usually comprises a light source for excitation, means for separating the excitation photons from the emission photons, a lens system for capturing the photons and, in general, imaging means.

Fluorescence techniques can be used with different types of microscopes, notably:

- A conventional optical microscope where the excitation light may pass through the sample or the lens. In the latter case, this is epifluorescence microscopy;
- A confocal microscope, for example by laser scanning that in particular enables three-dimensional images of the sample;
- A total internal reflection fluorescence microscope (usually called TIRF), which uses an evanescent wave to excite the fluorescence that is of only a very shallow depth, immediately adjacent to the interface of the sample substrate (usually glass) and of the liquid medium (usually water), in which the sample is disposed. Lighting is performed by a laser beam incident at a supercritical angle to create an evanescent wave (exponentially decreasing orthogonally to the interface).

TIRF microscopy, although currently booming and allowing precise observations, has some disadvantages. Indeed, the use of an adapted laser source is costly and the excitation field thus generated may not be homogeneous (due to interference from the coherence of the beam). In addition, lighting by the lens does not allow a homogeneous excitation and the resulting depth of penetration is not constant across the field to be observed. Moreover, there are containment losses of the excitation field related to the intrinsic light scattering by the cells.

FR-A-2943428 discloses a method of observation by fluorescence microscopy of a sample comprising fluorescent components in a liquid medium of refractive index $n_L$ arranged on a transparent support of refractive index $n_s$, which is greater than $n_L$ and less than or equal to 1.55, and an observation device comprising a full-field immersion lens, whose numerical angular aperture, ON, is greater than or equal to 1.33 and less than or equal to $n_s$, and a set of lenses for forming an image in at least one image plane, and which further comprises a mask arranged in the rear focal plane of the immersion lens or a conjugate plane of said rear focal plane, so as to obscure the fluorescence emission components of the sample in the angular directions in which the angle θ is less than or equal to a critical angle $θ_c$, with $θ_c$=arcsin $(n_L/n_s)$, and the angle θ defined as the angle of an angular direction of the fluorescence emission relative to the perpendicular direction of the support surface on which the sample to be observed is arranged.

This observation method permits obtaining high-quality fluorescence images with a low-cost device or improving the quality of images obtained by TIRF microscopy.

The device and the method described above lead to very satisfactory images with good resolution. Nevertheless, in certain circumstances, one may wish to improve the resolution.

SUMMARY OF THE INVENTION

The present invention aims to provide an alternative method permitting in particular to improve substantially the image resolution at the cost of some changes.

The solution of the invention is a method for observing an emission of light from a sample in a medium of refractive index $n_L$, the sample being placed against a surface of a transparent support of refractive index $n_s$, which is greater than $n_L$, wherein the light emission comprises luminous components of a given amplitude and phase, oriented toward the support and forming an angle θ with a direction perpendicular to the surface, including, on the one hand, supercritical luminous components, for which the angle θ is strictly greater than a critical angle $θ_c$=arcsin $(n_L/n_s)$, and, on the other hand, critical or subcritical luminous components, for which the angle θ is less than or equal to the critical angle $θ_c$, whereby the method implements an observation device capable of:

- Capturing at least part of the light emitted from a region of interest of the sample and obtaining a captured luminous signal that comprises luminous components emitted from the supercritical luminous components of the light emission;
- Applying filters to the captured luminous signal in order to selectively decrease the amplitude and/or change the phase of certain luminous components of the captured luminous signal in order to obtain a filtered luminous signal; and
- Transforming the filtered luminous signal into an image zone of the region of interest of the sample; wherein:
- A modulation of the filtered luminous signal is realized, wherein luminous components arising from the critical or subcritical luminous components of the light emission are allowed to pass through in order to obtain image zones from one and the same region of interest of the sample, the modulation pertaining to all or some of the captured luminous signal's luminous components emitted from the supercritical luminous components of the light emission; and
- at least one useful image zone of the sample is produced by combining image zones, wherein the combination evidences differences between the image zones pertaining to the modulation.

The light emitted by the sample may result from fluorescence (after an appropriate excitation) or from diffusion. A portion of this light is captured by an observation device, then filtered and converted into an image zone.

The region of interest of the sample is the part of the sample that is to be observed. It can be extended or isolated. In the latter case, it is possible to reconstruct a larger image by scanning the sample. An image zone is an image of a region of interest of the sample. It may thus be a full image of the sample, an image of a portion of the sample, or even an image of a point of the sample. The modulation applies to image zones issued from one and the same region of interest of the sample.

With the device according to the invention, it is possible to obtain microscopy images with an improved resolution, allowing for example to obtain valuable information for the study of biological materials.

The resolution improvement is obtained not by working directly on a luminous signal purged of all or part of the components arising from the light emitted by the sample at critical or subcritical angles, that is to say a signal rich in components arising from the light emitted by the sample at supercritical angles (the method described in the document FR-A-2943428), but rather by working indirectly, by a modulation of the signal applied to the components arising from the light emitted by the sample at supercritical angles. The method is indirect because it requires taking several image zones of the sample and combining them to obtain a useful image zone that evidences the differences between the image zones created by the modulation of the luminous signal at the origin of the image zones.

The modulation being applied to all or some of the luminous components of the captured luminous signal arising from the supercritical luminous components of the light emission, the combination enhances these supercritical luminous components in the useful image zone. By contrast, the components of the captured luminous signal arising from the light emitted by the sample at critical or subcritical angles not being altered by the modulation, the combination reduces these critical or subcritical components in the useful image zone. The combination can be seen as a demodulation. It shows in the useful image zone the contribution of the modulated supercritical components.

The modulation can affect the amplitude and/or the phase of the luminous components of the captured luminous signal. In other words, the filters used alter the amplitude and/or phase of the light waves. This is also the meaning of the verb "to act," when it is used relating to the filters in this application. To act differently, for two filters, means "to achieve a modulation." Changing the amplitude can be a more or less strong attenuation going up to full obscurement. Some of the filters used (but not all) can be neutral and not act; in this case, the resulting luminous signal is called a "filtered signal" anyway, even if it is identical to the captured luminous signal. "Passing" luminous components means that after filtering, the components remain, even though in an attenuated form (reduced amplitude) or with a modified phase.

The image zones, just like all images formed using a sensor such as a camera, contain information on the luminous intensity related to the square of the module of the filtered luminous signal.

Unexpectedly, the obtained resolution of the useful image zone can be improved by a factor of about 20 to 25%, especially if the modulation is applied to all the luminous components of the captured signal arising from the supercritical luminous components of the light emission (see the explanation of FIG. 7 below) with respect to an image zone obtained by the method of the document FR-A-2943428.

Taking image zones, in order to obtain a useful image zone, can be done simultaneously, for example by splitting the captured luminous signal and applying a filter to each split signal. Taking image zones can also be done successively. A luminous signal is then captured and filters are successively applied to it thus realizing the modulation. An image zone is stored for each filtered luminous signal obtained.

The method provides at least one useful image zone, but it can be applied as often as necessary, at a rate permitted by the observation device and the filters used, so as to obtain useful image zones at given time intervals. If the image zones correspond to points of the sample, a spatial scanning of the sample can be achieved.

The invention allows obtaining image zones with high sensitivity, especially zones localized at the interface between the support of refractive index $n_s$ and the medium of refractive index $n_L$. One can thus visualize events occurring near this interface to a certain depth. For an interface of glass/water (about $n_L$=1.33 and $n_S$=1.51), the depth may be about ⅙ of the wavelength, or less if only collecting the steeper luminous components (the most supercritical ones) of the emitted light, of the order from 50 nm (nanometers) to 100 nm for wavelengths in the visible zone.

Supports commonly used in microscopy, in particular fluorescence, are made of glass, and it is possible to choose conventional types of glass, of a refractive index less than or equal to 1.55, the cost of which is low, or glass types of a higher index.

Fluorochrome behaves as an antenna capable of transmitting a signal. This transmitter has in its immediate environment (a few tens of nanometers) electromagnetic components, which are evanescent when placed in a homogeneous medium. These components may become propagative when the fluorochrome is positioned near an interface. They then propagate at angles that are larger than the critical angle in the medium with the highest refractive index.

FIG. 5a shows the components of the emission of fluorescence of a transmitter 12 located at the interface between a support 20 and a liquid medium 11.

The fluorescence emission of the transmitter 12 comprises a component 14 emitted for θ between 0 and $θ_c$, and a component 15 emitted for θ greater than $θ_c$, called "no-light" or "supercritical light" and corresponding to evanescent components in the liquid medium 11 and that become propagative in the transparent support 20.

For example, for a glass/water interface, we find that the supercritical light can be up to about a third of the intensity of the total light emitted.

The value of the critical angle is given by the Snell-Descartes laws of refraction, where $θ_c$=arcsin $(n_L/n_s)$. In the case where the liquid is water ($n_L$=1.33) and the support is standard glass ($n_s$=1.52), $θ_c$ is 61°.

FIG. 5b shows the components of the emission of fluorescence of a transmitter 12 located at a greater distance of about 100 nm.

It has been found that the emitted light comprises the same component 14, issued with θ between 0 and $θ_c$, but no longer comprises components emitted at an angle greater than $θ_c$, corresponding to the supercritical light.

The method according to the invention allows to retrieve the information contained in the supercritical light and thus to produce useful image zones with information on structures and their possible evolution in the 100 nm depth from the liquid medium/support interface.

The numerical aperture, ON, of a lens is defined by ON=n·sin($\alpha_{max}$), where n is the index of the operating environment of the lens and $\alpha_{max}$ is the maximum collection angle of the lens.

Current commercial lenses with high numerical apertures with oil immersion (n=1.51) have been developed. They have ON, for example, of 1.45 and 1.49. The maximum captured angles are greater than the critical angle $\theta_c$. Thus, these lenses can collect most part of the supercritical light. Preferably, these lenses are corrected for spherical and chromatic aberrations and thus permit obtaining an excellent-quality full-field image.

According to particular embodiments of the invention, the invention may implement one or more of the following characteristics:

The luminous components of the captured luminous signal that are subject to said modulation are emitted from supercritical luminous components of the light emission for which the angle $\theta$ is within a predetermined range in accordance with a range of depths to be explored in the sample.

The image zones obtained by using the observation device and producing, by combination, the useful image zone of the sample are successively obtained by successively applying filters to the captured luminous signal.

The method may comprise the following steps:

a) taking a plurality of image zones in the same region of interest of the sample using the observation device and a plurality of filters, each filter used for taking an image zone of said plurality of image zones, the plurality of filters being such that:

A filter of said plurality of filters allows the passing through of, in the filtered luminous signal, luminous components arising from the supercritical luminous components of the light emission;

The filters of said plurality of filters all allow the passing through of luminous components of the captured luminous signal emitted from critical or subcritical components of the light emission and act in a substantially identical fashion between them on the luminous components of the captured luminous signal arising from the critical or subcritical luminous components of the light emission, and There are at least two filters of said plurality that act in a substantially different fashion between them on the amplitude or the phase of at least part of the luminous components of the captured luminous signal arising from supercritical luminous components of the light emission; and b) producing a useful image zone of the sample by a calculation combining the plurality of image zones taken in step a) in order to evidence differences between the image zones of the plurality of image zones of the sample.

The method may comprise the following steps:

a) taking at least two image zones of one and the same region of interest of the sample using the observation device and two filters, each filter used for taking one of the two image zones, the two filters being such that:

One of the two filters lets luminous components arising from the supercritical luminous components of the light emission pass through in the filtered luminous signal; and The other filter acts in a substantially identical fashion to said one of the two filters on the luminous components of the captured luminous signal arising from the critical or subcritical luminous components of the light emission and it decreases, to a substantially greater degree than said one of two filters, the amplitude of at least part of the luminous components of the captured light signal arising from the supercritical luminous components of the light emission; and b) producing a useful image zone of the sample by a calculation combining the two image zones of the sample taken in step a), the calculation comprising an algebraic difference between the two image zones of the sample.

The filters implemented also partially reduce the amplitude of all or some of the luminous components of the captured luminous signal arising from the critical and subcritical luminous components of the light emission.

Luminous components of the captured luminous signal arising from the luminous components of the light emission at the same angle $\theta$ are processed in a substantially identically fashion by a same filter for the reduction of the amplitude or the change of the phase.

The sample displaying a phenomenon to be observed with a given characteristic time, the image zones are successively taken at time intervals of less than or equal to half the characteristic time.

One of the image zones of the sample is obtained using a neutral filter that allows to pass through, in the filtered luminous signal and without any decrease of amplitude, all the luminous components of the captured luminous signal arising from the supercritical luminous components of the light emission; and another image zone of the sample is obtained with a total filter, which cancels in the filtered luminous signal all the luminous components arising from the supercritical luminous components of the light emission.

The observation device comprises a full-field immersion lens and the filters are located in a rear focal plane of the immersion lens and/or in a conjugate plane of said rear focal plane.

The filters comprise a diaphragm which, in an open position, allows the passing through of luminous components from the captured luminous signal arising from the supercritical luminous components of the light emission and that, depending on the degree of closure, allows the obscuring of the luminous components of the captured luminous signal arising from the supercritical luminous components of the light emission, having an angle $\theta$ greater than a limit value related to said degree of closure.

The sample to be observed is biological in nature.

According to a particular embodiment, the modulation does not affect all the luminous components of the captured luminous signal arising from the supercritical luminous components of the light emission. It may affect only those for which the angle $\theta$ is within a predetermined set, for example, the interval [$\theta_a$, $\theta_b$], $\theta_a$ and $\theta_b$ being both strictly greater than $\theta_c$. This allows the exploring of the range of corresponding depths in the sample (see explanation for FIG. 1).

In another embodiment, the method includes a step a) of taking a plurality of image zones corresponding to modulated luminous signals. For the modulation, it is necessary that at least one of the filters used allows the passing through of luminous components from the supercritical part of the light emission. It is also necessary that the other filters act differently from this filter on all or part of the supercritical components of the captured luminous signal. "Differently" can mean that the filters in question attenuate more, or less, the amplitude of the luminous components involved. The difference may also relate to the phase. The actions on the amplitude and phase can be combined.

On the other hand, the filters must act in a substantially identical manner on the luminous components arising from the critical or subcritical part of the light emission. The luminous components arising from the critical or subcritical part of the light emission can be changed by the filters used for obtaining the image zones, but this change should be substantially the same for all the combined image zones in order to get the useful image zone. "Substantially the same" means that in a particular embodiment, there is no difference, but, according to another embodiment, there may be minor differences from the desired modulation (the modulation of the luminous components arising from the supercritical luminous components of the light emission). Preferably, luminous components arising from the critical or subcritical luminous components of the light emission will be left in the filtered luminous signal.

The method comprises a step b), where image zones taken in step a) are combined. The combinations are made by a calculation based on the light intensity. This calculation is based on the filters used and is used to evidence the differences between the image zones caused by the modulation.

The advantage of taking a plurality of image zones is to reduce any background noise, for example by introducing averages in the calculation.

For example, one can take three successive image zones of a same region of interest of the sample. The first one is an image zone of the sample that contains information related to all the luminous components arising from the supercritical part of the captured signal, that is to say, the filter used has not substantially modified these components. The second one is an image zone that contains no information related to the luminous components from the supercritical part of the captured signal, that is to say, the filter used has obscured these components. The third image zone is taken under conditions identical to the first image zone. A possible combination of these three successive image zones is to compute the absolute value of the difference between, firstly, an average of the first and third image zones and, secondly, the second image zone. This can allow the reduction of noise in the useful image zone (photo-bleaching phenomenon, changes in excitation intensity, movement of the sample).

The images contain information related to the (positive) intensity of the overall electric field. A difference between two pixels can thus be positive or negative, which is why an absolute value is used to obtain a positive result that represents an intensity, namely that of the useful image zone.

According to another particular embodiment, in step a) two image zones are taken of one and the same region of interest of the sample. The first one is taken using a filter that allows the passing through of luminous components from the supercritical part of the light emission. The second one is taken using a filter that acts differently from the first filter upon all or part of the supercritical components of the captured signal, and substantially identically upon the critical or subcritical components of the captured signal. In step b), the two image zones are combined by computing for each pixel the absolute value of the difference between the first and the second image zones. This result represents an intensity, namely that of the useful image zone. The advantage of this embodiment lies in the simplicity of the combination of the image zones, that is to say, the simplicity and speed of the calculations.

According to a particular embodiment, one can reduce in the two image zones, in an identical fashion, part or all of the luminous components of the captured luminous signal arising from the critical or subcritical luminous components of the light emission. This is important when the light originating from the subcritical rays is very intense compared with that originating from the supercritical rays.

In general, the filters used respect the symmetry of revolution and treat in the same way the luminous components of the captured luminous signal arising from the luminous components of the light emission forming the same angle θ. Indeed, a modulation on the azimuth of the components of the light emitted does not present much interest. On the contrary, not modulating the azimuth prevents the introduction of astigmatism into the useful image zone.

If the sample changes over time (such as a cell membrane) with a given characteristic time, one takes successive image zones (rather representative of the sample in depth) with a period shorter than half the characteristic time (video frame rate) in order to monitor these changes. The method normally allows the obtaining of useful image zones (rather representative of the sample interface) at the same rate as that of the successive image zones, i.e., at the video frame rate and not at half of the video frame rate as in the method described in the document FR-A-2943428.

The addition of a diaphragm in the rear focal plane of the lens and/or in a conjugate plane can be done easily and in particular can be implemented with commercial microscopes. The result is a device whose cost of the improvement is very modest.

The function of the diaphragm is to obscure the luminous components of the captured luminous signal arising from the luminous components of the light emission from the sample in angular directions θ greater than or equal to a certain angle depending on the aperture of the diaphragm. FIGS. 5a and 5b refer to the principles of fluorescence emission. An advantage of the method is that the subcritical information is always available in the image zones used for the combination. This information is often interesting, because it is connected to the innermost regions of the sample.

BRIEF DESCRIPTION OF THE DRAWINGS

Other features and advantages of the present invention will become apparent from the following description of non-limiting exemplary embodiments, with reference to the accompanying drawings, wherein:

FIG. 7 is a graphical representation of the light intensity of the spots obtained from a same test sample, firstly by the method described in the document FR-A-2943428 (obscuring of critical or subcritical components) and secondly by a method according to the invention (modulation applied to the supercritical components, and then demodulation).

For reasons of clarity, the dimensions of the various elements shown in these figures are not necessarily in proportion to their actual dimensions. In the figures, identical references correspond to identical elements.

DETAILED DESCRIPTION

Figure 1:
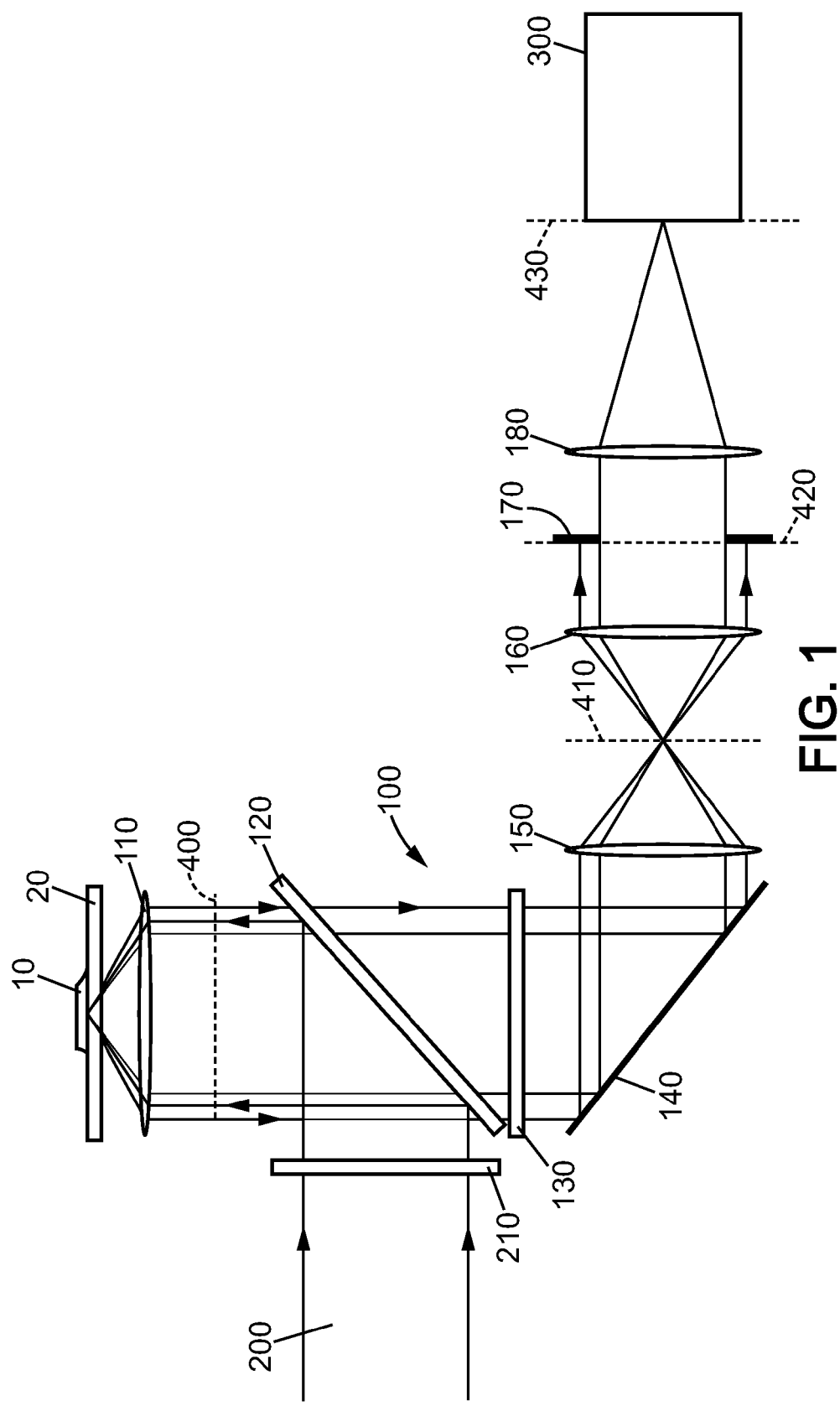
FIG. 1 shows a schematic view of a microscopy device allowing to implement a method according to the invention.

FIG. 1 shows a schematic view of a fluorescence microscopy device 100. It comprises an immersion lens 110, of which the ON is greater than or equal to 1.33. A glass support 20 is arranged above the immersion lens 110. Oil is disposed between the immersion lens 110 and the glass support 20.

A sample 10 to be observed is arranged on the glass support 20. This sample 10 comprises, for example, fluorescent elements dispersed in water.

The rear focal plane of the lens is referenced with number 400. Excitation light is generated by a beam 200 from a light source, which passes through an excitation filter 210 and is reflected by a dichroic mirror 120 to illuminate the sample 10 after passing through the transparent support 20. An example of the path of the incident excitation light is indicated by the arrows pointing to the top of the figure. The incident excitation light may be partly reflected and is then filtered by an emission filter 130 so that the image formed on an image plane comprises only the fluorescence light emitted by the sample 10.

The fluorescent light emitted by the sample 10 passes through the transparent support 20, the dichroic mirror 120, and the emission filter 130.

According to the embodiment shown in FIG. 1, this light is reflected off a mirror 140 and the rest of the device works with the reflected light.

A lens 150, called tube lens, allows the focusing of the light on an intermediate image plane 410.

Then the light is parallelized by a lens 160 and focused by a lens 180 onto the image plane 430, where the image is acquired by a suitable device, notably by a camera 300. The planes 430 and 410 are conjugate image planes of the observation plane.

The lenses 160 and 180 are arranged so that a conjugate plane 420 of the rear focal plane of the immersion lens 110 is located between the lenses 160 and 180.

A variable-aperture diaphragm 170 is arranged in the rear focal plane of the immersion lens. This diaphragm acts as a filter for the luminous components of the captured luminous signal. It can be in open position and allow the passing through of all the luminous components of the captured luminous signal arising from the luminous components of the light emission. It can be in a partially closed position and obscure part of the luminous components of the captured luminous signal.

More specifically, the light rays that are emitted following a certain angle by the fluorescent emitters of the sample 10 located in the observation plane intercept the rear focal plane 400 of the lens (or any conjugate plane 420 of the plane 400) at a certain distance $r(\theta)$ from the center (defined by the optical axis) of this plane. $r(\theta)$ is an increasing function of $\theta$. For aplanatic lenses, for example, $r(\theta)$ is approximately proportional to $\sin(\theta)$. Thus, all the rays emitted at the angle $\theta$ (conically) describe a circle of a radius of $r(\theta)$ in the rear focal plane.

When the diaphragm 170 is arranged in the rear focal plane 400 of the lens 110, the relationship between $r(\theta)$ and $\sin(\theta)$ is:

$r(\theta)=n_i \times f_o \times \sin(\theta)$, where $f_o$ is the focal distance of the immersion lens 110 (usually of the order of a few millimeters) and $n_i$ is the index of the immersion medium used for the lens (usually oil).

According to an embodiment, there is an immersion lens with a magnification G=100 and the focal distance of the tube lens 150 is $f_t$=200 mm.

We then have $f_o=f_t/G=2$ mm. In this configuration we get: $r(\theta_c)$=2.66 mm.

If the diaphragm 170 is arranged in the conjugate plane of the rear focal plane, one should take into account the magnification factor related to the optical system. For example, in the plane 420, it is necessary to introduce a multiplication factor G'=f160/f150 where f150 is the focal distance of the tube lens 150 and f160 is the focal distance of the lens 160.

The luminous components of the captured luminous signal arising from the critical or subcritical luminous components of the light emission intercept the rear focal plane following a closed centered disk of a radius of $r(\theta_c)$. The luminous components of the captured luminous signal arising from the supercritical luminous components of the light emission, where $\theta_c<\theta<\theta_{max}$, form an open ring in the rear focal plane $r(\theta_c)<r(\theta)<r(\theta_{max})$. The implementation of a diaphragm 170 centered on the optical axis and having an opening $r(\theta_c)$ thus allows to obscure all supercritical luminous components.

The selection is thus made at the emission. As a result, the lighting system does not need to be changed from that of a standard epifluorescence observation device. It is thus possible to illuminate with a source of non-coherent light, such as a standard white light, obtained in particular using a mercury lamp. This results in several advantages, such as the absence of significant additional cost (compared to TIRFM microscopy technique, where a laser light is required) as well as the possibility to obtain a homogeneous field (possibly allowing quantitative measurements).

According to one embodiment, actuation means of the diaphragm operate at the video frame rate (typically in the magnitude of a few tens of Hertz) in order to pass alternatively from the open position to the closed position with the speed of image acquisition. It is thus possible to have information on the volume and the surface simultaneously.

This imaging method is particularly suitable for imaging biological samples, in particular for the study of biological processes in living cells, such as cell adhesion phenomena, endocytosis/exocytosis, . . . .

Figure 2:
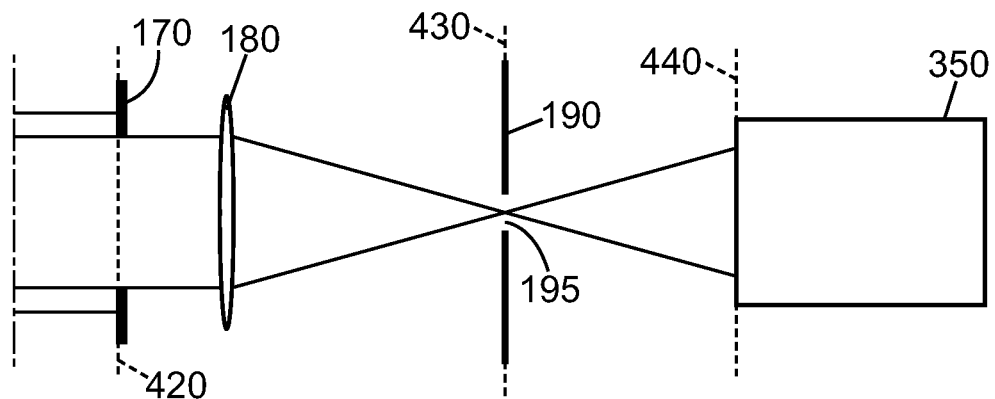
FIG. 2 shows a variant according to the invention of the apparatus shown in FIG. 1, suitable for confocal microscopy.

FIG. 2 shows a schematic view of a variant according to the invention of the device of FIG. 1 where the elements present before the image plane 430 are identical in both embodiments. In the device of FIG. 2, a pinhole-type mask 190 that comprises a hole 195 is arranged in the image plane. A mono-detector 350 allows a point-by-point acquisition of the light passing through the hole 195. It is thus possible to obtain a configuration that allows performing the confocal microscopy.

Figure 3:
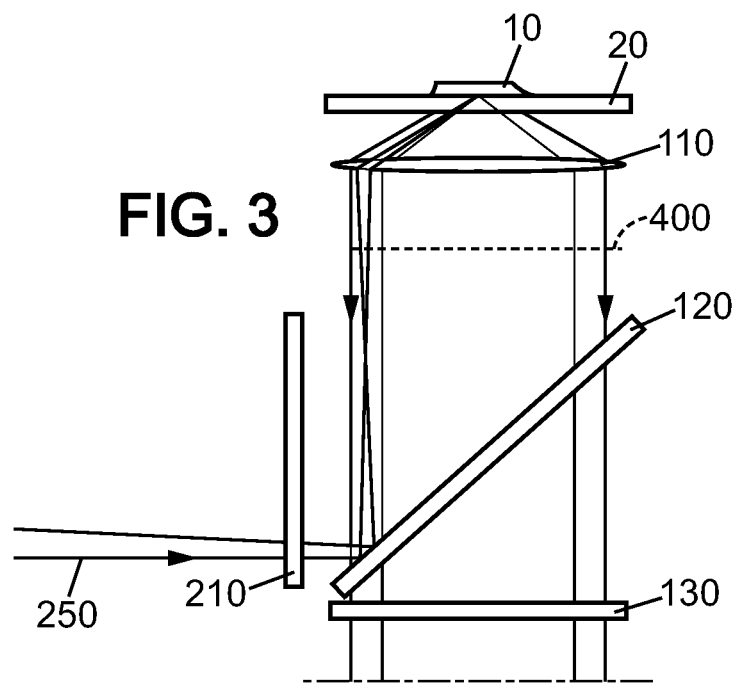
FIG. 3 shows a variant according to the invention of the apparatus shown in FIG. 1, suitable for TIRF microscopy.

FIG. 3 shows a schematic view of a variant according to the invention of the device of FIG. 1 where the elements of the microscopy device are similar, but where the light source differs.

In the device of FIG. 3, the light 250 is coming from a laser and the illumination of the sample is produced by total internal reflection. It is thus possible to obtain an improved TIRF type device.

Note that the rear focal plane of the commercial lenses is usually located inside the lens and is therefore difficult to access. It is thus often recommended to realize a system for imaging the rear focal plane to be able to insert the filter system 170 between the sensor and the lens.

According to one embodiment, an inverted fluorescence microscope of the Ti type of Nikon is used that comprises a module (ref. TI-T-BHP, MEB55810) that enables imaging the rear focal plane and positioning an annular mask to enable the (external) phase contrast with large numerical aperture lenses. It is possible to put into this type of module a diaphragm 170 of the device according to the invention. The system of centering and adjusting the position of the plane is quite suitable for a diaphragm filtering supercritical angles. The system comprises a plurality of positions for different lenses.

Figure 4:
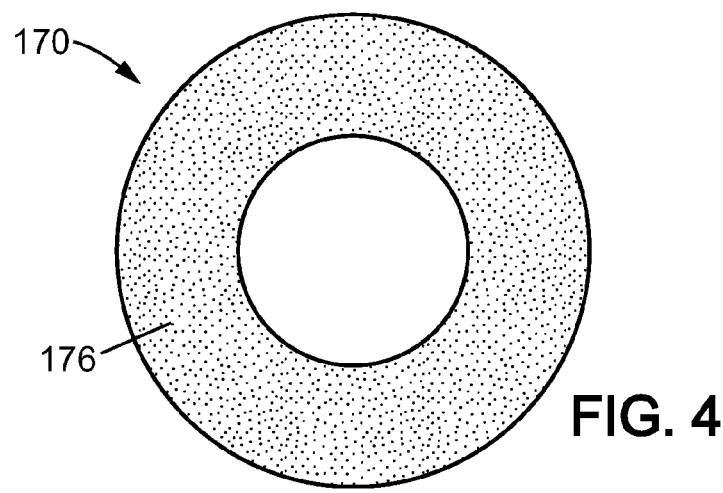
FIG. 4 shows an example of a filter for the implementation of a method according to the invention.
Figure 5A:
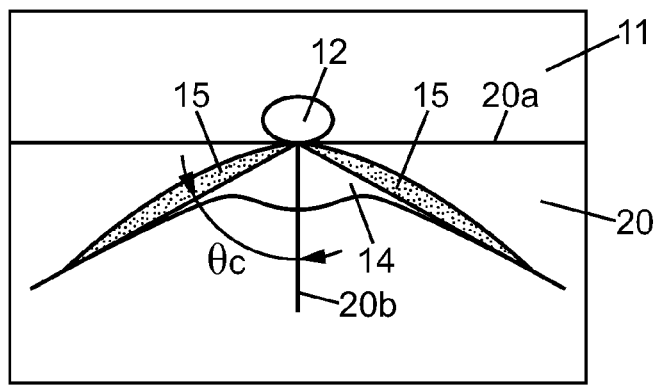
FIGS. 5a and b show the fluorescence emission components according to different configurations and have been commented on above.
Figure 5B:
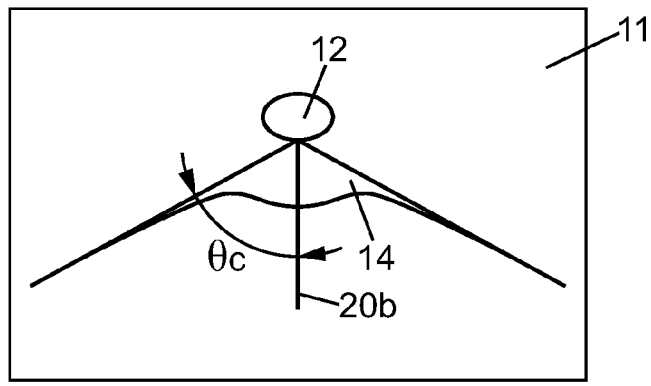

FIG. 4 shows a schematic view of a diaphragm 170 to be arranged in the rear focal plane 400 of the immersion lens 110 or in a conjugate plane 420 of said focal plane. The diaphragm 170 comprises a peripheral area 176 apt at obscuring light. This area 176 is either actually mobile (as in a camera), or the diaphragm is replaced by another, for example, by turning a motor-driven rotary filter wheel.

The diaphragm 170 may be an iris diaphragm, such as that sold by Thorlabs. Its aperture is adjusted by moving mechanical moving parts (not shown).

Another possibility is to use a wheel with openings or semi-transparent materials distributed on sectors of the wheel and rotate it. In this case, the diaphragm can, for example, be achieved by a circular hole of a suitable diameter in an opaque material. This allows the obtaining of very short transmission/shutter cycles, which, for example, keep pace with the acquisition pace of images with a camera.

According to one example of an embodiment, a Nikon "Ti-U"® type inverted fluorescence microscope is used with a base of the binocular tube of the phase "TI-T-BPH"®, an oil-immersion ×100 lens with a numerical aperture of 1.49. A fluorescence filter cube, which contains a transmission filter, a dichroic plate, and an excitation filter, is used. The light source used is a fiber source of the commercial reference "Nikon Itensilight"® with a 130 W Hg lamp and a generator "C-HGFI"®. The camera used is an EMCCD Andor Ixon+ camera, cooled to approximately −75°. The diaphragm 170 used is the iris diaphragm produced by Thorlabs.

The diaphragm is then positioned in the Nikon MEB55810 module ("TI-T-BPH") instead of the phase ring. The position of the diaphragm is adjusted by means of the Bertrand lens of the microscope and by displacement of the module by means of screws for centering and axial position. The procedure followed is the same as the adjustment of the phase ring supplied by the manufacturer with the module.

Observations have been conducted on embryonic human kidney cells marked by Choleratoxin (which binds to glycolipids on the membrane and the constituents of lipid rafts) coupled to Alexa 488 and excited by the Nikon Intensilight Hg 130 W lamp (conventional lamp). The filter cube used consists of an excitation filter with a bandwidth from 450 to 490 nm, a dichroic mirror of 500 nm, and an emission filter with a bandwidth from 510 to 550 nm.

Figure 6A:
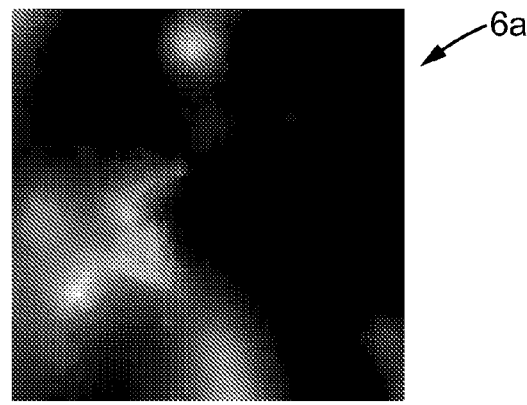
FIGS. 6a and 6b illustrate the image zones of a same cell respectively with and then without the luminous components of the captured luminous signal from the critical or subcritical luminous components of the light emission.
Figure 6B:
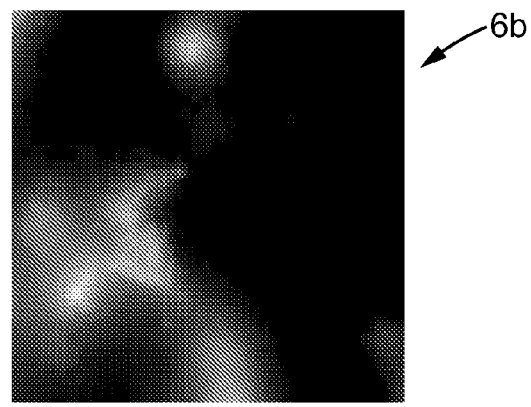
Figure 6C:
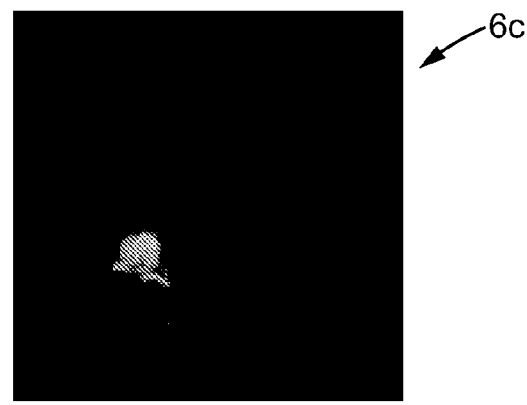
FIG. 6c shows a useful image zone of the same cell obtained by combining the image zones of FIGS. 6a and 6b.

FIGS. 6a and 6b show two images obtained with an open diaphragm (6a) and with a closed diaphragm to hide all the supercritical luminous components (6b). The pause time (T=300 ms) and the gain (G=0) are identical for images 6a and 6b. The image 6c is obtained as the absolute value of the difference between the images 6a and 6b (that is to say, between the intensity of the signals associated with the images).

It is noted that the two images 6a and 6b appear to be identical. However, image 6c is well contrasted. One advantageously observes intensity variations that are associated with membrane phenomena that are difficult to distinguish in the other two images, because they are embedded among other information coming from the inside of the cell.

It should be noted that these observations have been advantageously made with a "classic" lamp and that it was not necessary to implement a laser to obtain them.

Measurements of the lateral resolution have been performed with fluorescent beads Fluosphere® (marketed by Invitrogen) of the excitation/emission: 580/605 nm deposited by spin ("spin-coating") on a standard glass slide (thickness 0.13-0.16 mm), and then immersed in distilled water.

FIG. 7 illustrates the profile of the fluorescence intensity of these beads (normalized signal intensity on the ordinate as a function of lateral displacement on the abscissa, expressed in microns). It should be noted that the C2 profile, which corresponds to the useful image zone obtained by the method according to the invention is narrower than the C1 profile, which corresponds to the image obtained by the method described in document FR-A-2943428. The corresponding improvement in resolution is 20-25%.

The invention is not limited to these types of embodiments and should be interpreted in a non-limitative way and encompassing all equivalent embodiments.

The invention claimed is:

1. A method for observing a light emission of a sample in a medium with a refractive index $n_L$, the sample being arranged on a surface of a transparent support of refractive index $n_s$, which is greater than $n_L$, the light emission comprising luminous components of a given amplitude and phase, oriented toward the support and forming an angle θ with a direction perpendicular to the surface, said luminous components including supercritical luminous components, for which the angle θ is strictly greater than a critical angle $θ_c=\arcsin(n_L/n_s)$, and also including critical or subcritical luminous components, for which the angle θ is less than or equal to the critical angle $θ_c$, the method comprising:

capturing, using an observation device, at least part of the light emission from a region of interest of the sample and obtaining a captured luminous signal comprising luminous components arising from the supercritical luminous components of the light emission;

applying filters, using the observation device, to the captured luminous signal in order to selectively decrease the amplitude and/or change the phase of certain luminous components of the captured luminous signal to obtain a filtered luminous signal; and transforming, using the observation device, the filtered luminous signal into an image zone of the region of interest of the sample;

wherein:

the method realizes a modulation of the filtered luminous signal, in which luminous components arising from critical or subcritical luminous components of the light emission are allowed to pass through in order to obtain a plurality of image zones of one and the same region of interest of the sample, the modulation pertaining to all or some of the luminous components of the captured luminous signal arising from the supercritical luminous components of the light emission; and at least one useful image zone of the sample is produced by combining the plurality of image zones to produce at least one enhanced image zone for the region of interest, the combination evidencing differences between the image zones associated with the modulation.

2. The method according to claim 1, wherein the luminous components of the captured luminous signal being the subject of said modulation are emitted from the supercritical luminous components of the light emission for which the angle θ is within a predetermined range in accordance with a range of depths to be explored in the sample.

3. The method according to claim 1, wherein the image zones obtained by using the observation device and generating, by combining, the useful image zone of the sample, are successively obtained by successively applying filters to the captured luminous signal.

4. The method according to claim 1, the method further comprising:
a) taking a plurality of image zones in a same region of interest of the sample using the observation device and a plurality of filters, each filter being used to take one image zone of said plurality of image zones, the plurality of filters being such that:
a filter of said plurality of filters allows the passing through of, in the filtered luminous signal, luminous components arising from the supercritical luminous components of the light emission;
the filters of said plurality of filters all allow the luminous components of the captured luminous signal arising from the critical or subcritical luminous components of the light emission to pass through, and act substantially identically between them on the luminous components of the captured luminous signal arising from the critical or subcritical luminous components of the light emission; and
there are at least two filters of said plurality of filters that act substantially differently between them on the amplitude or the phase of at least some of the luminous components of the captured luminous signal arising from the supercritical luminous components of the light emission; and
b) producing a useful image zone of the sample by a calculation combining the plurality of image zones taken in step a) to evidence differences between the image zones of the plurality of image zones of the sample.

5. The method according to claim 1, the method further comprising:
a) taking at least two image zones of a same region of interest of the sample using the observation device and two filters, each filter being used to take one of the two image zones, the two filters being such that:
one of the two filters allows the passing through, in the filtered luminous signal, of the luminous components from the supercritical luminous components of the light emission; and
the other filter acts substantially identically to said one of the two filters on the luminous components of the captured luminous signal arising from the critical or subcritical luminous components of the light emission, and decreases substantially more than said one of the two filters the amplitude of at least some of the luminous components of the captured luminous signal arising from the supercritical luminous components of the light emission; and
b) producing a useful image zone of the sample by a calculation combining the two image zones of the sample taken in step a), wherein the calculation comprises an algebraic difference between the two image zones of the sample.

6. The method according to claim 1, wherein the filters used also partially reduce the amplitude of all or some of the luminous components of the captured luminous signal arising from the critical and subcritical luminous components of the light emission.

7. The method according to claim 1, wherein luminous components of the captured luminous signal arising from luminous components of the light emission that form the same angle θ are processed substantially identically by a same filter for decreasing the amplitude or changing the phase.

8. The method according to claim 1, wherein the sample showing a phenomenon to be observed having a given characteristic time, the image zones are successively taken at time intervals of less than or equal to half of the characteristic time.

9. The method according to claim 1, wherein:
one of the image zones of the sample is obtained using a neutral filter that allows to pass through, in the filtered luminous signal and without any decrease of amplitude, all the luminous components of the captured luminous signal arising from the supercritical luminous components of the light emission; and
another image zone of the sample is obtained with a total filter, which cancels in the filtered luminous signal all the luminous components arising from the supercritical luminous components of the light emission.

10. The method according to claim 1, wherein the observation device comprises a full-field immersion lens and the filters are located in a rear focal plane of the immersion lens and/or in a conjugate plane of said rear focal plane.

11. The method according to claim 10, wherein the filters comprise a diaphragm that allows, in an open position, the passing through of luminous components of the captured luminous signal arising from the supercritical luminous components of the light emission and allows, depending on a degree of closure of the diaphragm, to obscure the luminous components of the captured luminous signal arising from the supercritical luminous components of the light emission having an angle θ greater than a limit value related to said degree of closure.

12. The method according to claim 1, wherein the sample to be observed is biological.

13. A method for observing a light emission of a sample in a medium having a refractive index $n_L$, the sample being arranged on a surface of a transparent support having a refractive index $n_S$, the refractive index $n_S$ being greater than the refractive index $n_L$, the light emission being oriented toward the transparent support and forming an angle θ with a direction perpendicular to the surface, the light emission comprising supercritical luminous components for which the angle θ is greater than a critical angle $\theta_c = \sin^{-1} n_L/n_S$, critical luminous components for which the angle θ is equal to the critical angle $\theta_c$, and subcritical luminous components for which the angle θ is less than the critical angle $\theta_c$, the method comprising:
capturing at least a portion of the light emission from a region of interest of the sample to obtain a captured luminous signal, the captured luminous signal comprising the supercritical luminous components, the critical luminous components, and the subcritical luminous components;
applying filters to the captured luminous signal to selectively decrease an amplitude and/or change a phase of certain luminous components of the captured luminous signal to obtain a filtered luminous signal;

modulating the filtered luminous signal to obtain a first image zone of the region of interest of the sample by allowing luminous components arising from at least the supercritical luminous components and the subcritical luminous components to pass through an aperture of a diaphragm;

modulating the filtered luminous signal to obtain a second image zone of the region of interest of the sample by obscuring luminous components arising from the supercritical luminous components with the diaphragm and allowing luminous components arising from at least the subcritical luminous components to pass through the aperture of the diaphragm; and combining at least the first image zone and the second image zone to obtain at least one useful image zone of the region of interest of the sample, the combination evidencing differences between the first image zone and the second image zone associated with the modulation.

14. The method of claim 13, modulating the filtered luminous signal to obtain the first image zone comprising allowing luminous components arising from the critical luminous components to pass through the aperture of the diaphragm.

* * * * *